United States Patent [19]

Cornils et al.

[11] 4,102,913

[45] Jul. 25, 1978

[54] PROCESS FOR THE CONTINUOUS MANUFACTURE OF α-CYANO-ETHYLATED ALIPHATIC ALDEHYDES

[75] Inventors: Boy Cornils; Hans Feichtinger, both of Dinslaken; Willi Nöllen, all of Germany

[73] Assignee: Ruhrchemie Aktiengesellschaft, Oberhausen, Fed. Rep. of Germany

[21] Appl. No.: 790,202

[22] Filed: Apr. 25, 1977

[30] Foreign Application Priority Data

May 4, 1976 [DE] Fed. Rep. of Germany ....... 2619580

[51] Int. Cl.$^2$ ................. C07C 120/00; C07C 121/20; C07C 121/34
[52] U.S. Cl. ........................... 260/465.1; 260/465.8 R
[58] Field of Search ................ 260/465.1, 465.8 R

[56] References Cited

U.S. PATENT DOCUMENTS

| | | | |
|---|---|---|---|
| 2,353,687 | 7/1944 | Bruson et al. | 260/465.1 |
| 2,409,086 | 10/1946 | Walker | 260/465.8 R |

OTHER PUBLICATIONS

Bruson, et al.; J.A.C.S., vol. 66 (1944), pp. 56–58.

*Primary Examiner*—Joseph Paul Brust
*Attorney, Agent, or Firm*—Burgess, Dinklage & Sprung

[57] ABSTRACT

A continuous process for the manufacture of α-cyano-ethylated aliphatic aldehydes by continuously passing acrylonitrile and aldehyde through a tubular reaction zone and therein contacting the same with an alkali hydroxide at a temperature between 20° and 120° C, the contact of the acrylonitrile and aldehyde with the alkali hydroxide being for a brief period of time and thereafter immediately separating the reaction product from the alkali hydroxide. Unreacted acrylonitrile and aldehyde can be recycled to the tubular reactor and additional alkali hydroxide can be added to make up for any losses.

10 Claims, 2 Drawing Figures

PROCESS FOR THE CONTINUOUS MANUFACTURE OF α-CYANO-ETHYLATED ALIPHATIC ALDEHYDES

BACKGROUND OF THE INVENTION

1. Field of the Invention

This invention relates to the manufacture of α-cyano-ethylated aliphatic aldehydes by reaction of acrylonitrile and an aldehyde in the presence of an alkali metal hydroxide. More particularly, this invention relates to a process wherein the acrylonitrile and aliphatic aldehyde are in contact with the alkali metal hydroxide for only a brief period of time and reaction product is separated from the alkali metal hydroxide and unreacted acrylonitrile and aliphatic aldehyde is recycled. The process is conducted in a tubular reaction zone which can be vertical or horizontal at a temperature of 20° to 120° C.

2. Discussion of the Prior Art

In the presence of alkaline catalysts, acrylonitrile reacts with aldehydes, the α-carbon atoms of which possess one or two hydrogen atoms, forming 3-substituted propionitriles (U.S. Pat. No. 2,353,687). This so-called "cyanoethylation" reaction also occurs with other compounds which have an active hydrogen atom. For example, 2-ethyl butyraldehyde and acrylonitrile react in the presence of catalytic amounts of 50 percent caustic potash solution forming 2-(β-cyanoethyl)-2-ethyl butyraldehyde. A yield of 76.6 percent results after a reaction period of 4.5 hours. (H. A. Bruson, Th. W. Riener, J. Am. Chem. Soc., 66, 57 [1944]). The reaction is strongly exothermal. Acetaldehyde reacts with acrylonitrile in the presence of a 50 percent caustic soda solution forming γ-formylpimelonitrile. For a yield of 40–50%, the reaction period amounts to 2–3 hours. Under the same conditions, propionaldehyde forms 4.9 percent 2-methyl-4-cyanobutyraldehyde (U.S. Pat. No. 2,409,086). 2,2-dimethyl-4-cyano-butyraldehyde is formed in up to 60 percent yield from the reaction between isobutyraldehyde and acrylonitrile.

The well-known processes for cyanoethylation of aliphatic aldehydes proceed with only moderate selectivity and require long reaction times, therefore considerably impairing the economic efficiency of the processes. This disadvantage can not be eliminated by an increase in the concentration of the catalyst, as the reaction becomes more violent leading to polymerization or condensation reactions of the alkali sensitive starting materials.

It is, therefore, an object of the invention to provide a process for the preparation of such cyanoethylated products in the shortest possible reaction time and with a high yield.

SUMMARY OF THE INVENTION

Broadly, this invention contemplates a process for the continuous manufacture of a α-cyano-ethylated aliphatic aldehydes which comprises continuously passing an aliphatic aldehyde and acrylonitrile through a tubular reaction zone containing an alkali metal hydroxide at a temperature of 20° to 120° C and maintaining the same therein for a brief period of time and thereafter removing reaction product from the tubular reaction zone and separating the same from the alkali metal hydroxide. Acrylonitrile and aliphatic aldehyde which is unreacted can be recycled to the tubular reaction zone together with additional alkali metal hydroxide to make up for any losses.

Surprisingly, the problems mentioned above with respect to the realization of relatively large quantities of α-cyano-ethylated aliphatic aldehydes in a short period of time is solved in accordance with the present invention by a continuous process for the manufacture of such α-cyano-ethylated aliphatic aldehydes by reaction of acrylonitrile and an aliphatic aldehyde. The process is conducted in the presence of an alkali metal hydroxide at a raised temperature and the acrylonitrile and aldehyde are brought in contact with one another and the alkali metal hydroxide for only a brief period of time. The process is conducted at a temperature of 20° to 120° C. At the termination of the process, the reaction product is separated immediately from the alkali metal hydroxide and, preferably, recycled together with additional alkali metal hydroxide to make up for any losses.

BRIEF DESCRIPTION OF DRAWINGS

Referring to the drawings herein.

DESCRIPTION OF SPECIFIC EMBODIMENTS

Figure 1:
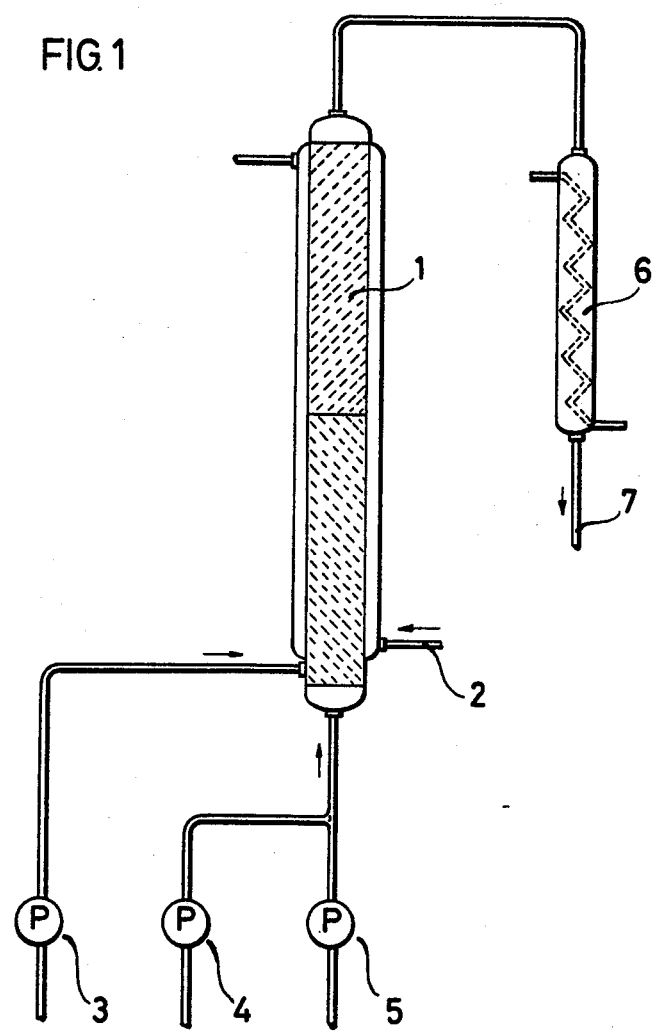
FIG. 1 is a flow diagram showing one mode for carrying out the continuous process of the invention.

Referring to FIG. 1, reference numeral 1 represents a vertically disposed tubular reactor surrounded by a jacket through which cooling water is introduced at point 2. Aqueous alkali metal hydroxide is introduced into the tubular reaction zone 1 via line 3, while acrylonitrile and aliphatic aldehyde are introduced separately therefrom through lines 4 and 5. Reaction product is removed from the top of the tubular reaction zone 1 and passes through a cooler 6. Product is recovered at receiver 7.

Figure 2:
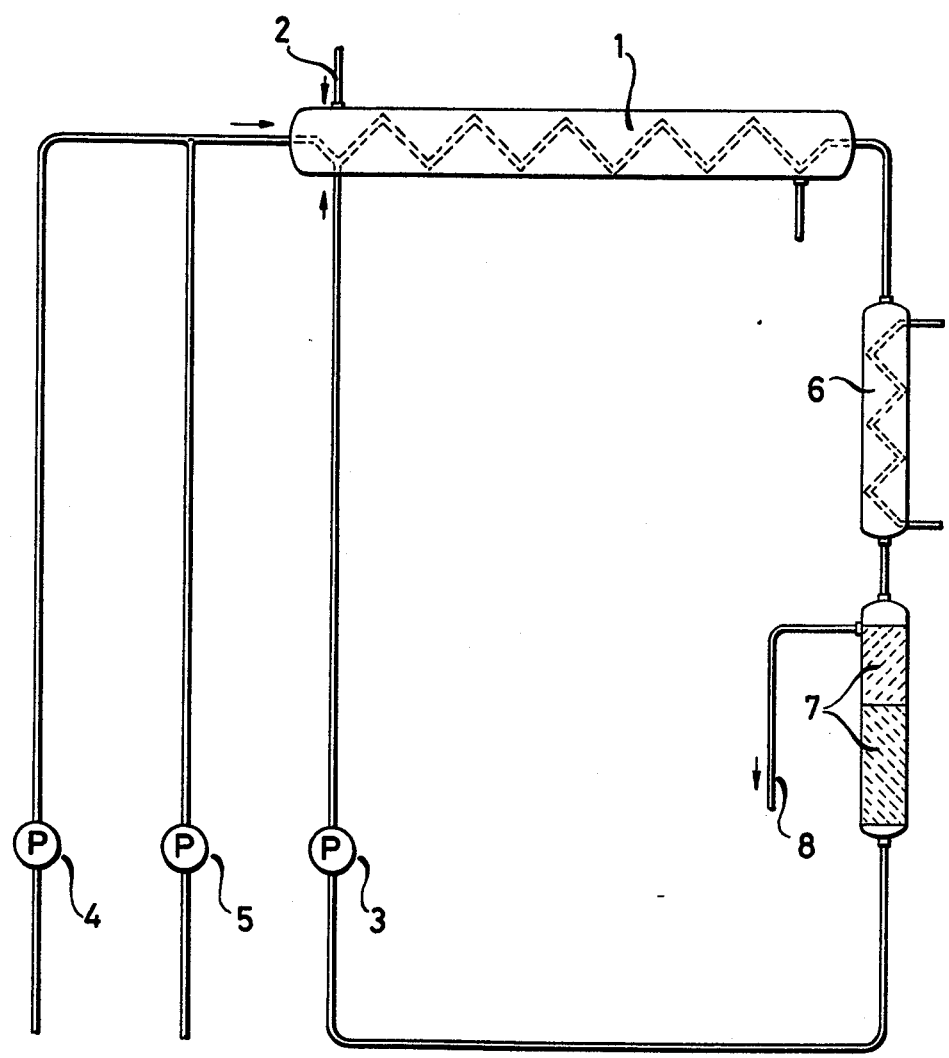
FIG. 2 is another schematic flow diagram showing another mode for carrying out the process of the invention.

An alternative mode for carrying out the process is shown in FIG. 2, wherein the tubular reactor 1 is horizontally disposed. The same is similarly equipped with a cooling jacket through which water is introduced at point 2. Acrylonitrile and aliphatic aldehyde are introduced through lines 4 and 5, while aqueous alkali metal hydroxide is introduced through line 3 together with recycled aqueous alkali metal hydroxide. Reaction product emanating from the right-hand side of the tubular reactor 1 passes through a cooler 6 where it enters a receiver 7. Organic reactants are withdrawn through line 8, permitting recycle of aqueous alkali metal hydroxide. The reactors, FIGS. 1 and 2, can be in the form of bubble column reactors or flow tubes, as these forms are among the most successful tubular reactors for use in accordance with the invention.

Acrylonitrile and aldehyde are usually employed in a stoichiometric ratio. When only one active hydrogen atom of the aldehyde reacts, then the molar ratio of the reaction partners is 1:1. If the aldehyde has two active hydrogen atoms on the carbon atom adjacent to the carbonyl group, then 2 mols of acrylonitrile can also be made to react with 1 mol of aldehyde. A small excess of one of the two reactants can be advantageous. For example, acrylonitrile and aldehyde can be employed in a molar ratio from 1.0:0.8 to 1.0:1.2. Correspondingly, the molar ratio can lie between 2.0:0.8 to 2.0:1.2 on employing 2 mols of acrylonitrile to one mol of aldehyde.

Aqueous solutions of alkali metal hydroxides can be used of concentration 20–80 percent, preferably 40–50 percent.

An essential feature of the procedure in accordance with the invention is that the acrylonitrile and aldehyde are brought into contact with the alkali metal hydroxide solution for a short period only. It has been found to be especially favorable to restrict the contact period to between 5 and 200 seconds, preferably 5 to 20 seconds.

During the actual conductance of the reaction in a bubble column reactor, the reactor is partly filled with an alkali metal hydroxide solution and heated to the required reaction temperature. Thereafter, acrylonitrile and aldehyde in liquid form, most suitably as a mixture, are allowed to flow through the diluted alkali metal hydroxide solution. The reaction product is deposited — if necessary after flowing through a cooling system — as a separate phase from the alkali metal hydroxide solution and is drawn off.

In another variation of the process according to the invention, the mixture of acrylonitrile and aldehyde and, separately, the diluted alkali metal hydroxide solution are introduced into a flow tube, heated to the reaction temperature. After flowing through a cooling system, the organic phase, the phase containing the reaction product and the awueous phase separate. The diluted phase is recycled after making up for any alkali metal hydroxide losses.

The cyano-ethylated products obtained, in accordance with the process of the invention, can generally be immediately processed further, without additional purification e.g. to diamines (FR-Pat. No. 1,521,134) or piperidines (GB-Pat. No. 1,307,065).

According to the process of the invention, the reaction with acrylonitrile is possible for a variety of aldehydes. For example: isobutyraldehyde, 2-ethylbutyraldehyde or 2-ethyl-hexanal. Generally, the aldehyde is a C 4 to C 12 aldehyde, saturated or not saturated.

In order to more fully illustrate the nature of the invention and the manner of practicing the same, the following examples are presented:

EXAMPLE 1

Continuous Manufacture of 2,2-dimethyl-4-cyanobutyraldehyde in the Bubble Column The apparatus is depicted in FIG. 1. A 30 – 50% NaOH solution is introduced into an externally heated glass vessel (internal diameter 31 mm, height 600 mm) with jacket. The solution occupies approx. a third of the reactor volume of 400 ml and can be continuously supplemented from supply tube 3, in accordance with requirements. The heating of the reactor tube occurs via a water circulation 2. Acrylonitrile and isobutyraldehyde are introduced into the base of the flow reactor from supply tubes 4 and 5 via two metering pumps. The specifically heavy caustic soda solution layer is bubbled through, then the reaction product collects in a liquid, upper phase which is continually drawn off via the cooler 6 to the receiver 7.

The addition product 2,2-dimethyl-4-cyanobutraldehyde is obtained in 80 – 85% yield in receiver 7. In the outline below, the analytical results from raw products (using various reaction temps.) which were obtained in the above way are reproduced. The residence time of the reactants in reactor 1 was about 7 seconds.

*Starting Materials:* 50% caustic soda solution; reaction temp.; choice between 20° to 50° C; mole ratio acrylonitrile:isobutyraldehyde as 1.1:1. Feed of acrylonitrile and isobutyraldehyde/hour: 280 ml.

| Temp. (° C) | Isobutyraldehyde | Acrylonitrile | Intermediate runnings | 2,2-dimethyl-4-cyano-butyraldehyde | Comp. | Last runnings |
|---|---|---|---|---|---|---|
| 20 | 11.7 | 31.3 | 0.7 | 33.6 | 2.3 | 20.4 |
| 30 | 7.7 | 9.8 | 1.5 | 62.3 | 3.2 | 15.5 |
| 40 | 4.6 | 4.4 | 0.7 | 67.8 | 5.6 | 17.4 |
| 50 | <0.1 | 3.8 | 1.0 | 84.1 | 3.6 | 7.5 |

Under these conditions the best results are obtained from the 50% catalyst solution.

The required 2,2-dimethyl-4-cyano-butyraldehyde was separated by means of a simple vacuum distillation.

EXAMPLE 2

Continuous Manufacture of Acrylonitrile-Addition-Products in a Flow Tube Reactor The apparatus is depicted in FIG. 2. A 50% caustic soda solution is introduced by means of a pump 3 into the horizontal flow tube reactor which is externally heated to 50° C. The heating medium is introduced at 2. The net internal volume of the tube reactor is 20 ml. A 300 ml mixture of acrylonitrile and isobutyraldehyde (molar ratio 1.1:1) is introduced under pressure, via pumps 4 and 5, every hour into the flow tube reactor. The volume ratio of the 50% caustic soda solution to the reaction mixture can be chosen arbitrarily. In the present example a volumetric ratio of (a) 1:3, (b) 2:3, (c) 1:1 was used. The residence time in the reactor is, depending on the chosen flow rate (a) 180 seconds, (b) 144 seconds, (c) 120 seconds.

The reaction products are removed via cooler 6. They are then separated using phase separator 7 into a lower specifically heavier caustic soda solution layer, which is recycled by pump 3, and into the upper product solution. The final product is drawn off at 8.

*Starting Materials:* 50% caustic soda solution; reaction temperature: 50° C; molar ratio acrylonitrile:isobutyraldehyde = 1.1:1. Hourly feed of acrylonitrile and isobutyraldehyde mixture: 300 ml. Residence time a) 180 seconds, b) 144 seconds, c) 120 seconds.

| Amount of caustic soda solution (ml/hour) | Isobutyraldehyde | Acrylonitrile | Intermediate runnings | 2,2-dimethyl-4-cyano-butyraldehyde | Comp. | Last runnings |
|---|---|---|---|---|---|---|
| a) 100 | <0.1 | 2.6 | 0.2 | 84.1 | 3.8 | 9.2 |

-continued

| Amount of caustic soda solution (ml/hour) | Analysis of crude product according to LGC(%) | | | | | |
|---|---|---|---|---|---|---|
| | Isobutyr-aldehyde | Acrylo-nitrile | Intermediate runnings | 2,2-dimethyl-4-cyano-butyr-aldehyde | Comp. | Last runnings |
| b) 200 | <0.1 | 4.9 | 0.1 | 81.1 | 7.6 | 6.3 |
| c) 300 | <0.1 | 5.5 | 0.8 | 78.1 | 2.6 | 13.0 |

EXAMPLE 3

In the apparatus (FIG. 2) 180 ml of 50% caustic potash solution is introduced hourly through pump 3 into the tube reactor heated to 60° C. At the same time, a 220 ml mixture of acrylonitrile and 2-ethylbutanal (molar ratio 1.1:1) is introduced per hour via pumps 4 and 5. After passing through the reaction zone the reaction product reaches the phase separator 7 via cooler 6. The resulting raw product separates as an oily phase above the KOH solution. The latter is recycled. The oily phase contains 85% 2-($\beta$-cyano-ethyl)-2-ethyl-butanal.

EXAMPLE 4

In the apparatus (FIG. 2) 180 ml of 50% caustic potash solution are reacted hourly in a co-current flow, at a temperature of 60° C, with 220 ml of a mixture of acrylonitrile and 2-ethylhexanal (molar ratio 1.1:1). After passing through the reaction zone a reaction mixture, which contains 92% 2-($\beta$-cyanoethyl)-2-ethyl-hexanal, is introduced into the phase separator.

What is claimed is:

1. In the $\alpha$-cyanoethylation of an aliphatic aldehyde by contacting acrylonitrile with an aliphatic aldehyde capable of cyanoethylation in the presence of an alkali metal hydroxide, the improvement which comprises carrying out the process continuously in a tubular reaction zone at a temperature of 20° to 120° C while maintaining the reactants therein in contact with the alkali metal hydroxide for between 5 and 200 seconds and thereafter removing reaction product and separating the same immediately from the alkali metal hydroxide.

2. A process according to claim 1 wherein the tubular reaction zone is a bubble column reactor.

3. A process according to claim 1 wherein the acrylonitrile and aldehyde are employed in a molar ratio of 1.0:0.8 to 1.0:1.2.

4. A process according to claim 1 wherein the acrylonitrile and aliphatic aldehyde are employed in a molar ratio of 2.0:0.8 to 2.0:1.2.

5. A process according to claim 1 wherein the alkali metal hydroxide is in the form of an aqueous solution having a concentration of 20 to 80 percent by weight.

6. A process according to claim 5 wherein the concentration of the alkali metal hydroxide in the aqueous solution is between 40 and 50 percent by weight.

7. A process according to claim 1 wherein the acrylonitrile and aldehyde are brought into contact with the alkali metal hydroxide for between 5 and 20 seconds.

8. A process according to claim 1 wherein the aliphatic aldehyde is selected from the group consisting of isobutyraldehyde, 2-ethyl-butyraldehyde and 2-ethylhexanal.

9. A process according to claim 1 wherein the aliphatic aldehyde is one whose alpha carbon atom has one or two hydrogen atoms.

10. A process according to claim 1 wherein the tubular reaction zone is a flow tube.

* * * * *